US006884616B1

(12) United States Patent
Négrier et al.

(10) Patent No.: US 6,884,616 B1
(45) Date of Patent: *Apr. 26, 2005

(54) DNA-CONSTRUCT FOR THE TISSUE-SPECIFIC EXPRESSION OF A BLOOD COAGULATION FACTOR

(75) Inventors: Claude Négrier, Irigny (FR); Marie Héléne Rodriguez, Lyon (FR); Nathalie Enjolras, Caluire (FR)

(73) Assignee: ZLB Behring GmbH, Marburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/559,344

(22) Filed: Apr. 27, 2000

(30) Foreign Application Priority Data

Apr. 27, 1999 (EP) .............................................. 99107397

(51) Int. Cl.⁷ .......................... C12N 15/63; C12N 15/00
(52) U.S. Cl. ................................ 435/320.1; 424/93.21; 435/69.1; 435/252.3; 435/440; 514/44; 514/802; 514/834
(58) Field of Search ...................... 424/93.21; 435/69.1, 435/320.1, 252.3, 440; 514/44, 802, 834

(56) References Cited

U.S. PATENT DOCUMENTS

| 5,565,358 A | 10/1996 | Marguerie de Rotrou et al. ........................ 435/320.1 |
| 6,066,778 A | * 5/2000 | Ginsburg et al. ............... 800/3 |

FOREIGN PATENT DOCUMENTS

| WO | WO 93/00438 | 1/1993 |
| WO | WO 94/29471 | 12/1994 |
| WO | WO 98/55639 | 12/1998 |

OTHER PUBLICATIONS

Romp et al. Platelets contain releasable coagulatin factor IX antigen. (1993) Blood Coagulatoin and Fibrinolysis, vol. 4, pp. 90 910.*
Wang et al. Persistent Systemic Production of Factor IX in Mice by Skeletal Myoblast–Mediated Gene Transfer: Feasability of Repeat Application to Obtain Therapeutic Levels. (1997) Blood vol. 90, No. 3, pp. 1075–1082.*
Anderson. Human Gene Therapy. (1998) Nature vol. 392 (6679 Suppl.) pp. 25–30.*
Somia and Verma. Gene Therapy: Trials and Tribulations. (2000) Nature Reviews/Genetics, vol. 1, pp. 91–99.*
Verma and Somia. Gene therapy–promises, problems, and prospects. 1997, Nature, vol. 389, pp. 239–242.*
Uzan et al. Tissue Specific Expression of the Platelet GPIIb Gene, 1991, J. Biol. Chem. vol. 266, No. 14, pp. 8932–8939.*
Hao et al. Expression of Biologically Active Human Factor IX in Human Hematopoietic Cells after Retroviral Vector–Mediated Gene transduction, 1995, Human Gene Therapy, vol. 6, pp. 873–880.*

Jallat, Sophie et al., "Characterization of Recombinant Human Factor IX Expressed in Transgenic Mice and in Derived Trans–Immortalized Hepatic Cell Lines," The EMBO Journal, vol. 9, No. 10, pp. 3295–3301, (1990).
Kurachi, Sumiko et al., "Role of Intron I in Expression of the Human Factor IX Gene," Journal of Biological Chemistry, vol. 270, No. 10, pp. 5276–5281, (Mar. 10, 1995).
Rodriguez, H., Abstract—XP-000938902—"Tissue Specific Expression of Factor IX in HEL Cells," Blood, vol. 94., No. 10 (Nov. 15, 1999).
Uzan, Georges et al., "Regulation of Gene Transcription During the Differentiation of Megakaryocytes", Thrombosis and Haemostasis, vol. 74, pp. 210–212 (1995).
Kurachi, Kotoku et al., "Regulatory Mechanism of the Factor IX Gene", Thrombosis and Haemostasis, vol. 73, pp. 333–339 (1995).
Salier, Jean–Phillippe et al., "Functional Characterization of the 5'–Regulatory Region of Human Factor IX Gene", The Journal of Biological Chemistry, vol. 265, No. 12, pp. 7062–7068 (Apr. 25, 1990).
Camerino, G. et al., "Regional Localization on the Human X Chromosome and Polymorphism of the Coagulation Factor IX Gene (Hemophilia B Locus)", Proc. Natl. Acad. Sci., vol. 81, pp. 498–502 (Jan. 1984).
Yoshitake, Shinji et al., "Nucleotide Sequence of the Gene for Human Factor IX (Antihemophilic Factor B)", Biochemistry, vol. 24, pp. 3736–3750 (1985).
Boyd, Y. et al., "Assignment of the Haemophilia B (Factor IX) Locus to the q26–qter Region of the X Chromosome", Ann. Hum. Genet., vol. 48, pp. 145–152 (1984).
Roberts, Harold R., "Molecular Biology of Hemophila B", Thrombosis and Haemostasis, vol. 70, pp. 1–9 (1993).
Nakai, Hiroyuki et al., "Adeno–Associated Viral Vector–Mediated Gene Transfer of Human Blood Coagulation Factor IX into Mouse Liver", Blood, vol. 91, No. 12, pp. 4600–4607 (Jun. 15, 1998).
White, Steve J. et al., "Long–Term Expression of Human Clotting Factor IX From Retrovirally Transduced Primary Human Keratinocytes In Vivo", Human Gene Therapy, vol. 9, pp. 1187–1195 (May 20, 1998).
Baru, Moshe et al., "Retroviral–Mediated in Vivo Gene Transfer into Muscle Cells and Synthesis of Human Factor IX in Mice", Intervirology, vol. 38, pp. 356–360 (1995).

(Continued)

Primary Examiner—Jon Weber
Assistant Examiner—Holly Schnizer
(74) Attorney, Agent, or Firm—Finnegan, Henderson, Farabow, Garrett and Dunner, L.L.P.

(57) ABSTRACT

A DNA-construct has been disclosed which is suitable for a tissue-specific expression of a blood coagulation factor like Factor IX, which comprises a DNA coding for an amino acid sequence of a blood coagulation factor and a DNA coding for a promoter which is specific for the expression in hematopoietic cells.

9 Claims, 12 Drawing Sheets

OTHER PUBLICATIONS

Wang, Jian–Min et al., "Persistent Systemic Production of Human Factor IX in Mice by Skeletal Myoblast–Mediated Gene Transfer: Feasibility of Repeat Application to Obtain Therapeutic Levels", Blood, vol. 90, No. 3, pp. 1075–1082 (Aug. 1, 1997).

Cherington, Van et al., "Retroviral Vector–Modified Bone Marrow Stromal Cells Secrete Biologically Active Factor IX in Vitro and Transiently Deliver Therapeutic Levels of Human Factor IX ato the Plasma of Dogs After Reinfusion", Human Gene Therapy, vol. 9, pp. 1397–1407 (Jul. 1, 1998).

Hao, Qian–Lin et al., "Expression of Biologically Active Human Factor IX in Human Hematopoietic Cells After Retroviral Vector–Mediated Gene Transduction", Human Gene Therapy, vol. 6, pp. 873–880 (Jul. 1995).

Martin, Paul et al., "HEL Cells: A New Human Erythroleukemia Cell Line With Spontaneous and Induced Globin Expression", Science, vol. 216, pp. 1233–1235 (Jun. 1982).

Tabilio, A. et al., "Expression of Platelet Membrane Glycoproteins and α–Granule Proteins by a Human Erythroleukemia Cell Line (HEL)". EMBO J. vol. 3, pp. 453–459 (1984).

Long, Michael W. et al., "Regualtion of Megakaryocyte Phenotype in Human Erythroleukemia Cells", Clinical Investigation, vol. 85, pp. 1072–1084 (Apr. 1990).

Nishizuka, Yasutomi, "The Roll of Protein Kinase C in Cell Surface Signal Transduction and Tumour Promotion", Nature, vol. 308, pp. 693–698 (Apr. 19, 1984).

Hong, Ying et al., "Inhibition of Protein Kinase C Suppresses Megakaryocytic Differentiation and Stimulates Erythroid Differentiation in HEL Cells", Blood, vol. 87, No. 1, pp. 123–131 (Jan. 1, 1996).

Haas, Thomas A. et al., "Integrin–Ligand Interactions: A Year in Review", Current Opinion in Cell Biology, vol. 6, pp. 656–662 (1994).

Uzan, Georges et al., "cDNA Clones for Human Platelet GPllb Corresponding to mRNA From Megakaryocytes and HEL Cells", Eur. J. Biochem., vol. 171, pp. 87–93 (1988).

Frachet, Philippe et al., "GPllb and GPllla Amino Acid Sequences Deduced From Human Megakaryocyte cDNAs", Molecular Biology Reports, vol. 14, pp. 27–33 (1990).

Prandini, M.H. et al., "Isolation of the Human Platelet Glycoprotein llb Gene And Characterization of the 5' Flanking Region", Biochemical and Biophysical Research Communications, vol. 156, No. 1, pp. 595–601 (Oct. 14, 1988).

Bray, Paul F. et al., "Platelet Glycoprotein llb", J. Clin. Invest., vol. 80, pp. 1812–1817 (Dec. 1987).

Uzan, Georges et al., "Tissue–Specific Expression of the Platelet GPllb Gene", The Journal of Biological Chemistry, vol. 266, No. 14, pp. 8932–8939 (May 15, 1991).

* cited by examiner

ß-Gal transient expression directed by GPIIb in HeLa cells
(panel A) and HEL cells (panel B)

Transient FIX production under CMV promoter control in HEL cells after PMA 1nM induction (pcDNA3 was used as reference for statistics (* represents p<0.05)

Stable expression of GPIIb-FIX(WT) and GPIIb-FIX(WT.I1) constructs in HEL cells (culture without PMA). pcDNA3-GPIIb/FIX(WT) was used as reference for statistics (** $p<0.01$; * $p<0.05$)

FIG.10

FIX procoagulant activity from PMA-stimulated GPIIb-FIX(WT.I1) expressing HEL cells. The values represent the mean of 3 individual experiments.

FIG. 11

DNA-CONSTRUCT FOR THE TISSUE-SPECIFIC EXPRESSION OF A BLOOD COAGULATION FACTOR

INTRODUCTION

Subject of the invention is a DNA-construct for the tissue-specific expression of a blood coagulation factor.

It is known that Factor IX (FIX) is a vitamin-K dependant glycoprotein which is produced by hepatocytes and secreted into the blood circulation (Kurachi et al., 1995; Salier et al., 1990). The FIX gene is located on the X-chromosome and contains 8 exons and 7 introns (Camerino et al., 1984; Boyd et al, 1984; Yoshitake et al., 1985). Absence or deficiency of Factor IX causes a severe bleeding disorder called hemophilia B (Roberts et al., 1993).

Hemophilia B is a disorder arising from modifications of a single known gene. It was therefore early proposed as a potential target for gene therapy. The cells chosen as target have to be easily accessible for gene transfer and need to be able to express Factor IX at a significant level. In these target cells, the FIX molecule needs to be modified to become an active coagulation factor (γ-carboxylation and cleavage of the propeptide). Several potential target cells were tested such as hepatic cells (Nakai et al., 1998), keratinocytes (White et al., 1998), muscle cells (Baru et al., 1995; Wang et al., 1997), or bone marrow stromal cells (Cherington et al., 1998). In vitro, the human myeloid leukemia cell line (HL60) transfected with a retroviral vector bearing a human FIX cDNA was shown to be able to produce a biologically active FIX (Hao et al., 1995). This invention is directed to the expression of blood coagulation factors in hematopoietic cells and specificially in platelets.

As hematopoietic cells the human erythroleukemia cell line HEL has already been used which mainly expresses an erythroid phenotype (Martin et al., 1982) but also some megakaryocytic markers like platelets membrane glycoproteins (Tabilio et al., 1984). After induction by phorbol-12-myristate-13-acetate (PMA), HEL cell line expresses increased amounts of megakaryocytic proteins like glycoprotein IIb/IIIa complex, Platelet Factor 4, or von Willebrand Factor (Long and coll., 1990). The PMA effects are mediated via the activation of protein kinase C (Nishizuka et al., 1984; Hong et al., 1996).

The human platelet glycoprotein IIb (GPIIb) is the α subunit of the platelet integrin ?IIbβ3 also known as IIb-IIIa complex which functions as a specific receptor for fibrinogen, fibronectin and von Willebrand's factor (Haas and Plow, 1994). GPIIb cDNA was initially isolated from mRNA libraries from HEL cells and human megakaryocytes (Uzan et al., 1988; Frachet et al., 1990). The human GPIIb gene was identified by Prandini et al. (1988).

The tissue specificity of the GPIIb promoter was assessed using the chloramphenicol acetyltransferase (CAT) reporter gene. Under GPIIb promoter control, a CAT expression was only detected in the hematopoietic cell line HEL (Uzan et al., 1991).

In order to treat hemophilia B by gene therapy it is necessary to have a tissue-specific expression of Factor IX. The present invention provides a solution to the problem of expressing blood coagulation factors in such hematopoietic cells.

It has now been found that a DNA-construct is suitable for a tissue-specific expression of a blood coagulation factor if it comprises a DNA coding for an amino acid sequence of a blood coagulation factor and a DNA coding for a promoter which is specific for the expression in hematopoietic cells. The solution to the above-mentioned problem has been demonstrated with a DNA-construct wherein as promoter the DNA coding for the human platelet glycoprotein IIb (=GPIIb) has been used.

DETAILED DESCRIPTION

The development of said DNA-construct was performed as follows:

A. Construction of the Chimeric Molecules

1. Generation of the FIX cDNAs:

Wild type FIX gene contains 3 ATG codons in frame clustered at aminoacid -46, -41 and -39. In order to try to improve FIX production, five FIX cDNA expression vectors with different ATG sites have been produced, directed by the CMV promoter. The truncated FIX intron 1, previously shown to have an expression-increasing activity in HepG2 cell line (Kurachi et al., 1995) was cloned and introduced in FIX cDNAs. In an initial part of this project, stable transfections of CHO cells with CMV-FIX(-41S) and CMV-FIX (-41S.I1) constructs led to the best FIX production in the culture supernatants. These two constructs FIX(-41S) and FIX(-41S.I1) cDNAs which are bearing only the -41 ATG were therefore the first FIX constructs used to transfect the hematopoietic cell line. The modified 5'extremity of the F IX(-41S)cDNA (SEQ.ID.No.1) is

```
-41S: 5' TGGATCCTTGGAGCGCGTGAACATGATCTTGG 3'
           -46                -41    -39
```

However, all the results obtained with FIX(-41S) cDNAs were further confirmed with the FIX(WT) and FIX(WT.I1) cDNAs. The 5'extremity of FIX WT cDNA (SEQ.ID.No.2) is

```
WT: 5' TGGATCCATGCAGCGCGTGAACATGATCATGGCAGAA 3'
         -46               -41    -39
```

2. Generation of the GPIIb Promoter Vectors

The lineage-specific promoter GPIIb was chosen to express FIX transgenes in hematopoietic cells. The pBLCAT-GPIIb vector bearing the −643/+33 GPIIb promoter and the chloramphenicol acetyltransferase (CAT) reporter gene was obtained from G. Uzan.

Figure 1:
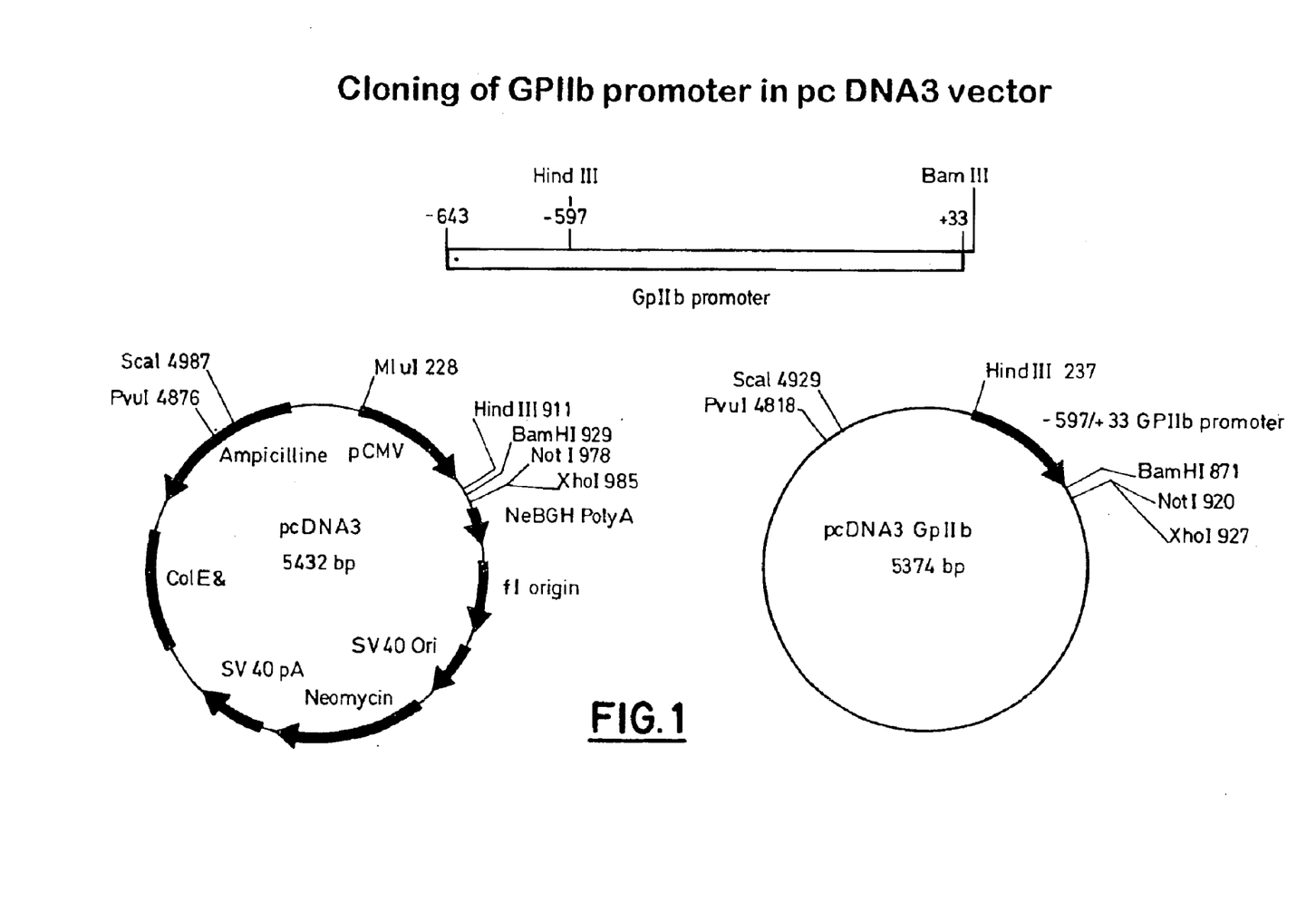
FIG. 1 illustrates the cloning of the GPIIb promoter into the pcDNA3 vector, thereby producing the pcDNA3-GPIIb construct.

In order to use pcDNA3 vectors (Invitrogen, the Netherlands) as an expression vector for FIX (which has more restriction enzyme sites and a neomycine resistance gene and appeared, therefore, more convenient for the next studies), the endogenous CMV promoter was replaced by the GPIIb promoter. This promoter was sorted from the pBLCAT-GBIIb vector after HindIII-BamHI digestion. This product encompassed −597 to +33 fragment of the GPIIb promoter (SEQ.ID.No.3) comprising the crucial domains for the promoter specificity (Uzan et al., 1991 and 1995). It was introduced in a CMV-deleted pcDNA3 opened by the same enzymes. The construct obtained was the so called pcDNA3-GPIIb (SEQ.ID.No.4 and FIG. 1). All the FIX cDNAs were sub-cloned in pcDNA3-GPIIb plasmid using BamHI-XhoI digestion.

3. Generation of the β-Galactosidase Vectors

Figure 2:
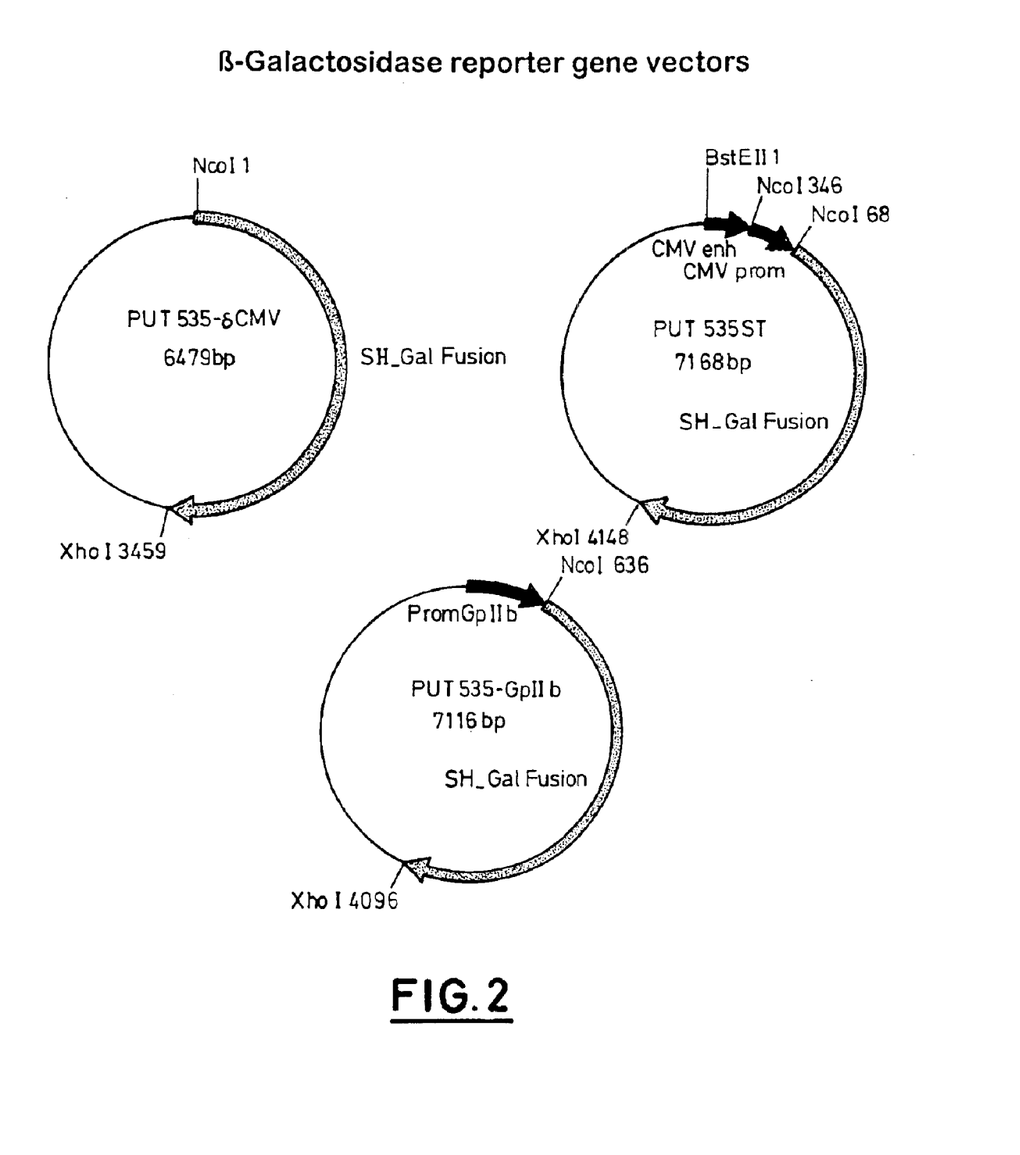
FIG. 2 demonstrates the generation of the pUT535-GPIIb construct, which contains a B-galactosidase reporter gene under the control of the truncated GPIIb promoter.

To test the activity of the truncated (−597/+33) GPIIb promoter in HEL cell line, the β-Galactosidase reporter gene was chosen. The pUT535 vector (Cayla, Toulouse, France) where the β-Gal gene expression is directed by the CMV promoter and enhancer (FIG. 2) was chosen. To exchange the CMV sequences by the truncated GPIIb promoter, the GPIIb promoter was digested by HindIII-BamHI, treated with Klenow DNA polymerase to obtain blunt extremities and then introduced in BstEII-NcoI-opened pUT535 treated with Klenow DNA polymerase. The GPIIb-β-Gal vector was named: pUT535-GPIIb (FIG. 2). The negative control plasmid (pUT535-δCMV) was the pUT535 deleted of the CMV sequences by BstEII-NcoI digestion.

B. Tissue-Specificity of the GPIIb Promoter in Hematopoietic Cells pUT535, pUT535δCMV and pUT535-GPIIb constructs were tested in two different cell lines: HEL and HeLa cells. The HEL cell line (Human Erythroleukemia Cells) is a classical cell line used to test megakaryocytic promoter expression. HeLa cells (Human cervix epitheloid carcinoma) are their classical negative control counter-part.

Materials and Methods:

HEL cells were maintained in RPMI/10% FCS medium with 5% $CO_2$. β-Gal vectors (2 μg DNA) were transfected in HEL cells (1×10$^6$ cells) using FUGENE™ 6 (Boehringer Mannheim). After overnight incubation, the cells were harvested and placed in 10 ml of RPMI/1% BSA (Boehringer, Mannheim). PMA (Sigma) was added to the medium in one of the two assays (final concentration: 1 nM). HeLa cells were maintained in DMEM-10% FCS with 5% $CO_2$. 90 mm Petri dishes with 5×10$^6$ cells were prepared the day before transfection. The cells were treated with 20 μg DNA and 20 μl Lipofectin™ reagent (Gibco) for 5 hours. After this incubation time, the cells were washed and placed in DMEM-1% BSA with or without PMA 1 nM. The cells were harvested 40 hours later, incubated with a lysis buffer, and the lysates were diluted to a final protein concentration of 1.5 mg/ml. The chemiluminescent β-Gal reporter Gene Assay kit (Boehringer Mannheim) was used as described by the manufacturer to quantify the β-galactosidase.

Figure 3:
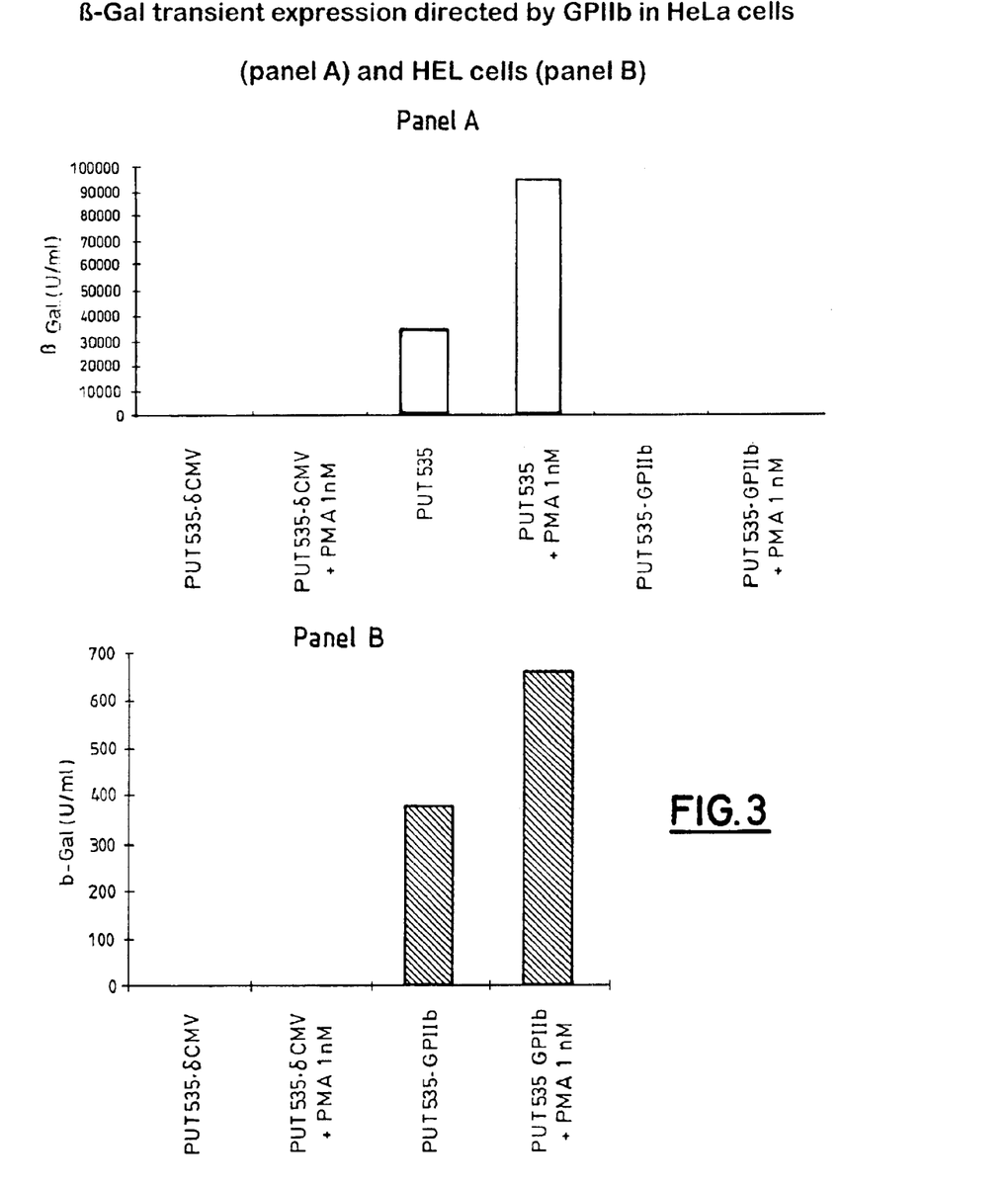
FIG. 3 shows the transient B-galactosidase expression directed by the CMV and GPIIb promoter in HeLa cells (Panel A) and shows the transient B-galactosidase expression directed by the CMV and GPIIb promoter in HEL cells (Panel B).

Results:

In HeLa cells, β-Gal reporter gene was expressed only when the cells were transfected with a vector containing the CMV promoter, without and with PMA induction. No β-Gal expression was found with the construct directed by GPIIb promoter (FIG. 3, panel A).

In HEL cells (FIG. 3, panel B), CMV gave the highest β-Gal production (Table 1 below). However, GPIIb promoter led to the production of a significant amount of β-Gal with an increase in production after PMA treatment. When the β-Gal amount obtained with pUt535 in HEL cells was taken as 100%, the β-Gal amount with truncated GPIIb promoter was 13% in the cells without PMA treatment. In comparison, Uzan et al. (1991) found that the CAT activity with the GPIIb promoter corresponded to 15% of the CAT activity obtained with the RSV promoter control in the same cell line.

TABLE 1

β-Gal activity in transiently transfected HEL cells

| | β-Gal | | | |
|---|---|---|---|---|
| | −PMA | | +PMA | |
| | U/ml | % | U/ml | & |
| CMV promoter | 2959 | 100 | 22910 | 100 |
| GPIIB promoter | 376 | 13 | 662 | 3 |

In conclusion, −597/+33 GPIIb promoter induced a tissue-specific expression of the reporter gene in the hematopoietic cell line since no β-Gal expression was detected in HeLa cells. In these transient transfections of HEL cells, β-Gal production obtained with this hematopoietic-specific promoter was low in comparison with the results measured with the CMV promoter. However, the results obtained in vitro are similar to the results published by Uzan et al. (1991).

C. FIX Transient Expression in HEL Cells

To test the possibility of producing FIX in hematopoietic cells, HEL cells were transiently transfected with FIX vectors bearing either CMV or GPIIb promoters, called CMV-FIX and GPIIb-FIX, respectively. The study was first done with the FIX(-41S) constructs and the results were confirmed with the FIX WT constructs.

1. Materials and Methods 7.5×10$^6$ HEL cells were transfected with 20 μg DNA using 20 μl Superfect Transfection reagent (Qiagen). After 6 hours, the cells were harvested and placed in RPMI/1% BSA±PMA 1 nM at a final concentration of 2.5×10$^5$ cells/ml. The supernatants were collected after 96 hours and the cells were numbered.

For the FIX WT constructs, pcDNA3-FIX WT and pcDNA3 WT.I1 have been transfected in HEL cells (1×10$^6$ cells) using 6 μg, Fugene 6 and 2 μg DNA. Following overnight incubation, the cells were harvested and placed in 5 ml of RPMI/1% BSA/PMA 1 nM for CMV-FIX transfections and in 2.5 ml of induction medium for the GPIIb-FIX transfections. Four days after transfection, the supernatants were recovered and the cells were numbered.

2. Results with FIX(-41S) Constructs

Figure 4:
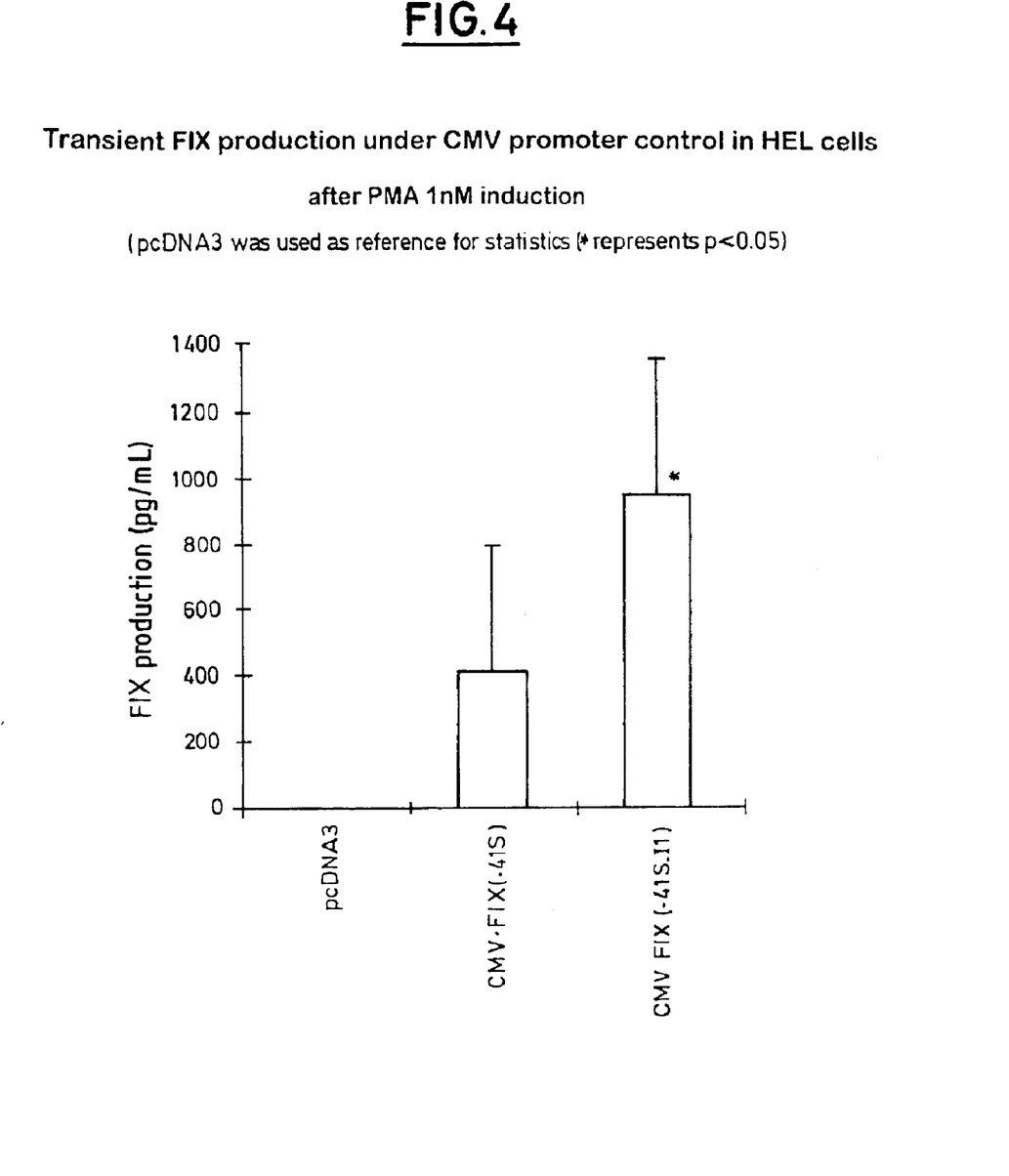
FIG. 4 shows the transient FIX production under CMV promoter control in HEL cells after PMA induction.

When the cells were incubated without PMA, the FIX production obtained with the CMV-FIX construct was very low and not accurately detectable by ELISA (Asserachrom FIX, Stago, Asnières, France). The results presented in FIG. 4 were obtained after induction with 1 nM PMA. Under CMV promoter control, FIX secretion by CMV-FIX (-41S)-transfected HEL cells was low (408.66 pg/ml) and not significant. The best production was obtained with the cells transfected with FIX(-41S.I1). The mean production was 2-fold higher than with FIX(-41S) cDNA and was significantly different from the result obtained with FIX(-41S) cDNA ($p<0.05$). A similar result was obtained when adjusting with the cell number. Indeed, HEL transfected with FIX(-41S.I1) produced $4.5 \pm 2.5$ ng/$1 \times 10^6$ cells and this result was significantly different from the result obtained with FIX(-41S)-transfected HEL cells ($1.5 \pm 0.9$ ng/$1 \times 10^6$ cells; $p<0.01$).

Similar experiments were done with the GPIIb-FIX constructs, and in this case ($2.5 \times 10^5$ cells/ml after transfection), the FIX production was too weak to be detectable in the supernatants. Microsep™ microconcentrators (Pall Gelman Sciences) with a 30Kd cut-off were used to concentrate the proteins. In the concentrated GPIIb-FIX(-41S.I1) supernatant obtained with, PMA-stimulated HEL cells, FIX protein was barely detectable. This result was in agreement with the results obtained with the β-Gal reporter gene (Table 1), confirming that the GPIIb potential was low in comparison with the CMV promoter.

3. Results with FIX WT Constructs

Figure 5:
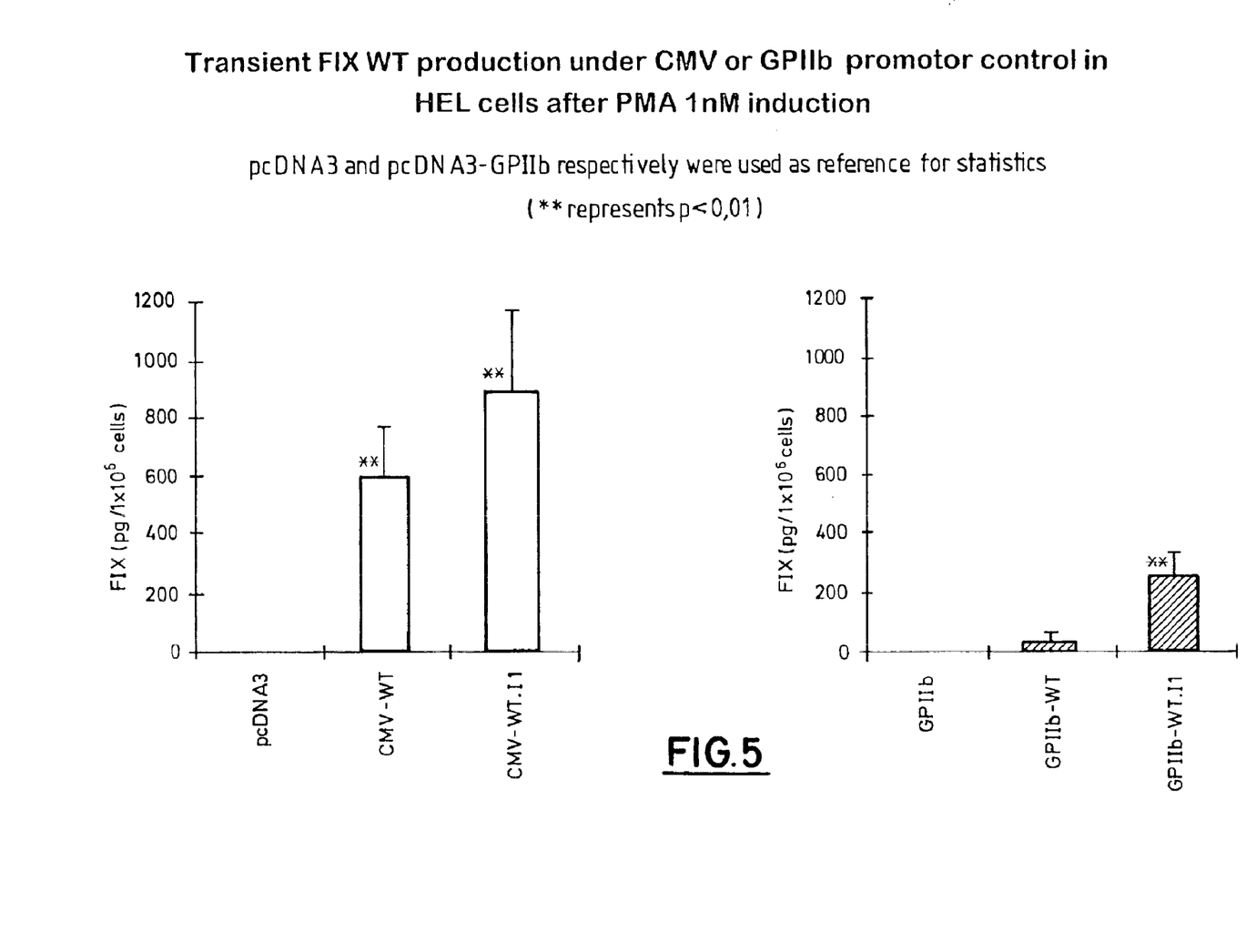
FIG. 5 demonstrates transient production of FIX WT under CMV or GPIIb promoter control in HEL cells after PMA induction.

FIG. 5 presents the FIX production obtained with the FIX WT. These results confirm that:

HEL cells are able to produce FIX after transient transfection.

The best production levels were obtained with FIX WT.I1 constructs and were significantly different from the corresponding FIX WT results.

After tansient transfections, the GPIIb promoter was less effective for FIX production than the CMV promoter in HEL cells. GPIIb-FIX WT.I1-transfected HEL cells produced about 30 percent of the FIX production obtained with the same cDNA under CMV promoter control ($257,71 \pm 85,38$ pg/$1 \times 10^6$ cells versus $881, 28 \pm 288,32$ pg/$1 \times 10^5$ cells).

D. FIX Expression in Stably Transfected HEL Cells

As mentioned above, in the transient expression system, a low FIX production was obtained. Therefore, cells stably expressing FIX were generated.

1. Materials and Methods

Cells: HEL cells ($1 \times 10^6$ cells) were transfected with 2 μg of Pvul linearized plasmid during 5 hours using FUGENE™ 6 transfection system (Boehringer, Mannheim). After incubation, the cells were harvested and placed in fresh medium supplemented with 0.6 mg/ml G418.

To compare FIX production, the G418-resistant cells were placed in RPMI/1% BSA supplemented with Vitamin K 1 ng/ml±PMA 1 nM ($2.5 \times 10^5$ cells/mL). After 1, 2, 3 or 4 days of incubation, the cells were numbered and the supernatants were frozen. FIX concentrations were measured using a FIX ELISA kit (Asserachrom FIX, Stago, Asnières, France).

Immunoblotting analysis: Supernatants (1 ml) were diluted fourfold in an equilibration buffer (Hepes 10 mM, KCl 100 mM, $MgCl_2$ 2 mM, Triton x100 0.1%). Fifty microliters of anti-human factor IX antibody bound to DEAE A50 Sephadex kindly provided by Centeon™ (USA) were added to the supernatant solutions and incubated 1 hr at 4° C. The DEAE was then collected by centrifugation (2 min at 2500 rpm) and washed three times with the equilibration buffer. Factor IX was eluted by Laemmli buffer (Laemmli, 1970). Samples containing Factor IX were subjected to electrophoresis on SDS-PAGE/10% polyacrylamide gel and semidry blotted onto Hybond™ C Pure membrane (Amersham). The blots were blocked with TBS-(0.15 M NaCl, 10 mM Tris-HCl, pH 7.5) Tween (0.1%) for 1 hr at room temperature and then incubated with 1:3,000 dilution of a polygonal rabbit anti-human FIX antibody (Dako™). The membrane was washed 3 times in TBS-T and then incubated with a 1:10,000 dilution of a peroxydase-labeled anti-rabbit antibody (Biorad) for 30 min. After washing 3 times, a chemiluminescent signal was detected by autoradiography using the ECL System (Amersham™).

Procoagulant activity: Factor IX activity was determined by a one-stage clotting assay. Fifty microliters of control plasma were diluted (1/10) in imidazole buffer (Diagnostica Stago, Asnieres, France). Fifty microliters of diluted supernatant were added to 50 μl of deficient Factor IX plasma (Immuno, Illkirch, France) and to 50 μl of Silimat® cephalin (Bio-merieux™, Marcy l'Etoile, France). After 4 min incubation at 37° C., clotting was initiated by addition of 50 μl of 50 mM $CaCl_2$ buffer. Coagulation times were measured in a STA Compact® coagulometer (Diagnostica Stago™ Asnières, France) and Factor IX activity was determined from a log-log standard curve.

FIX activation by factor XIa: FIX was immunoprecipitated and further activated in vitro by Factor XIa (Enzyme Research Lab., Swansea, UK) with a ratio enzyme/substrate of 1/40. Activation buffer consisted of Tris HCL 50 mM, NaCl 150 mM, $CaCL_2$ 5 mM, polyethylene glycon 0.01%, pH 7.5. Reactions were incubated for 30 nms and 1 hour at 37IC, and reated samples were thereafter diluted in Laemmli buffer.

Northern blot analysis: Total mRNAs were prepared from $7 \times 10^6$ stably transfected HEL cells usind the Rneasy Mini Kit (Qiagen, Courtaboeuf, France). After electrophoresis on 1.2% agarose gel in phosphate buffer (10 mM $NaH_2PO_4$, 10 mM $Na_2PO_4$, pH 7), mRNAs were transferred on a nylon membrane (Hybond N, Amersham, Les Ulis, France). RNA probes consisting of full length human factor IX or rat GAPDH were generated and labeled with NTP containing digoxigenin-UTP using the invitro transcription system with T7 RNA polymerase kit (Boehringer Mannheim Meylan, France). Follwing hybridization, the signals were detected by chemiluminescence using the DIG Luminescent Detection Kit from Boehringer Mannheim (Meylan, France).

Figure 6:
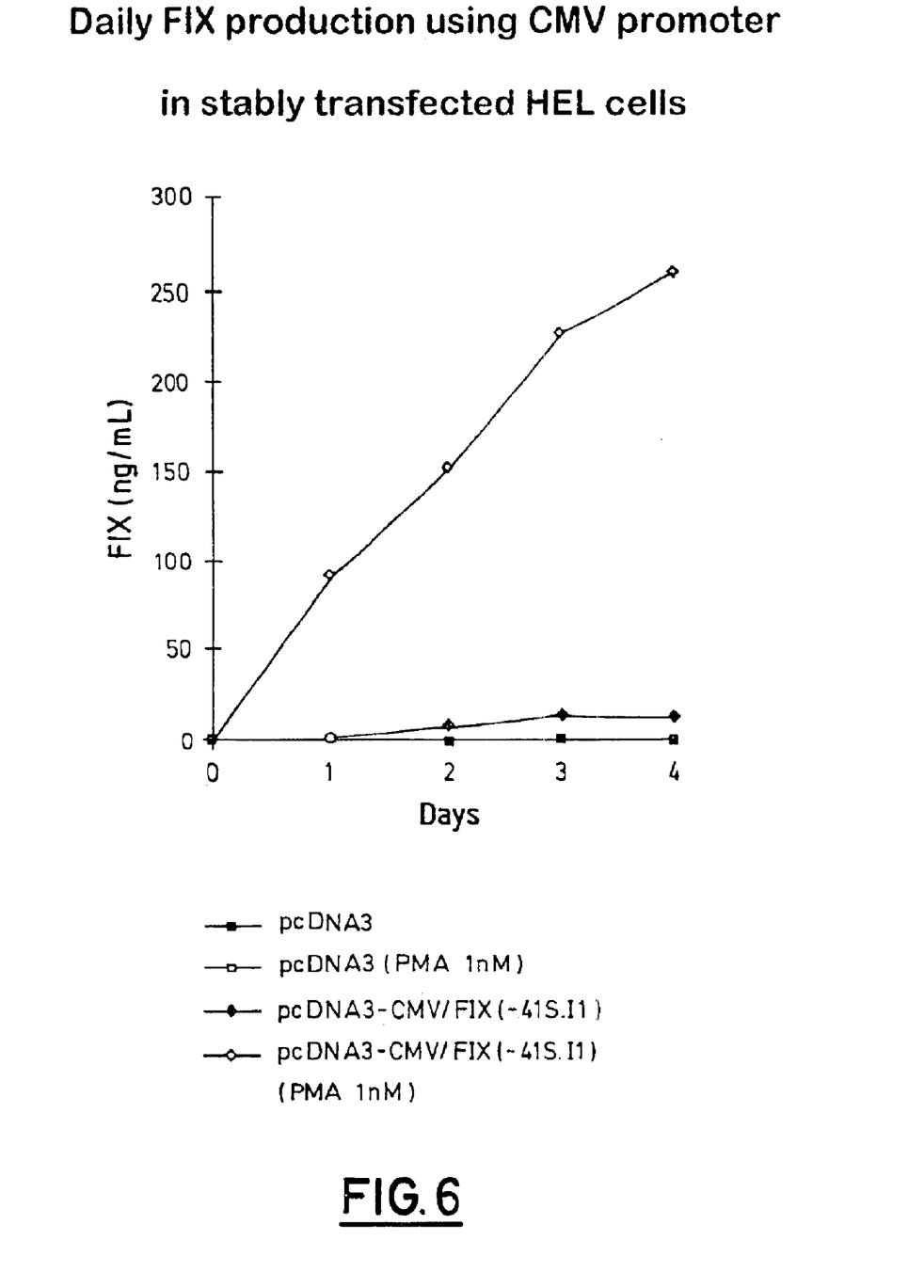
FIG. 6 demonstrates FIX production under CMV promoter control in stably transfected HEL cells.

2. Daily FIX Production of FIX(41S.I1) Expressing HEL Cells 2.1. CMV-FIX(-41S.I1) Transfected HEL Cells No FIX was detected in the supernatants of pcDNA3-transfected HEL cells (FIG. 6). After 4 days, 11,65 ng/ml of FIX were detected in the conditioned medium of the CMV-FIX(-41S.I1) transfected cells. Following PMA induction, FIX production (259,87 ng/ml) was 23-fold higher than the production obtained without PMA and was 250-fold higher than the result obtained with transient transfections.

2.2. GPIIb-FIX(-41S.I1) Transfected HEL Cells

Figure 7:
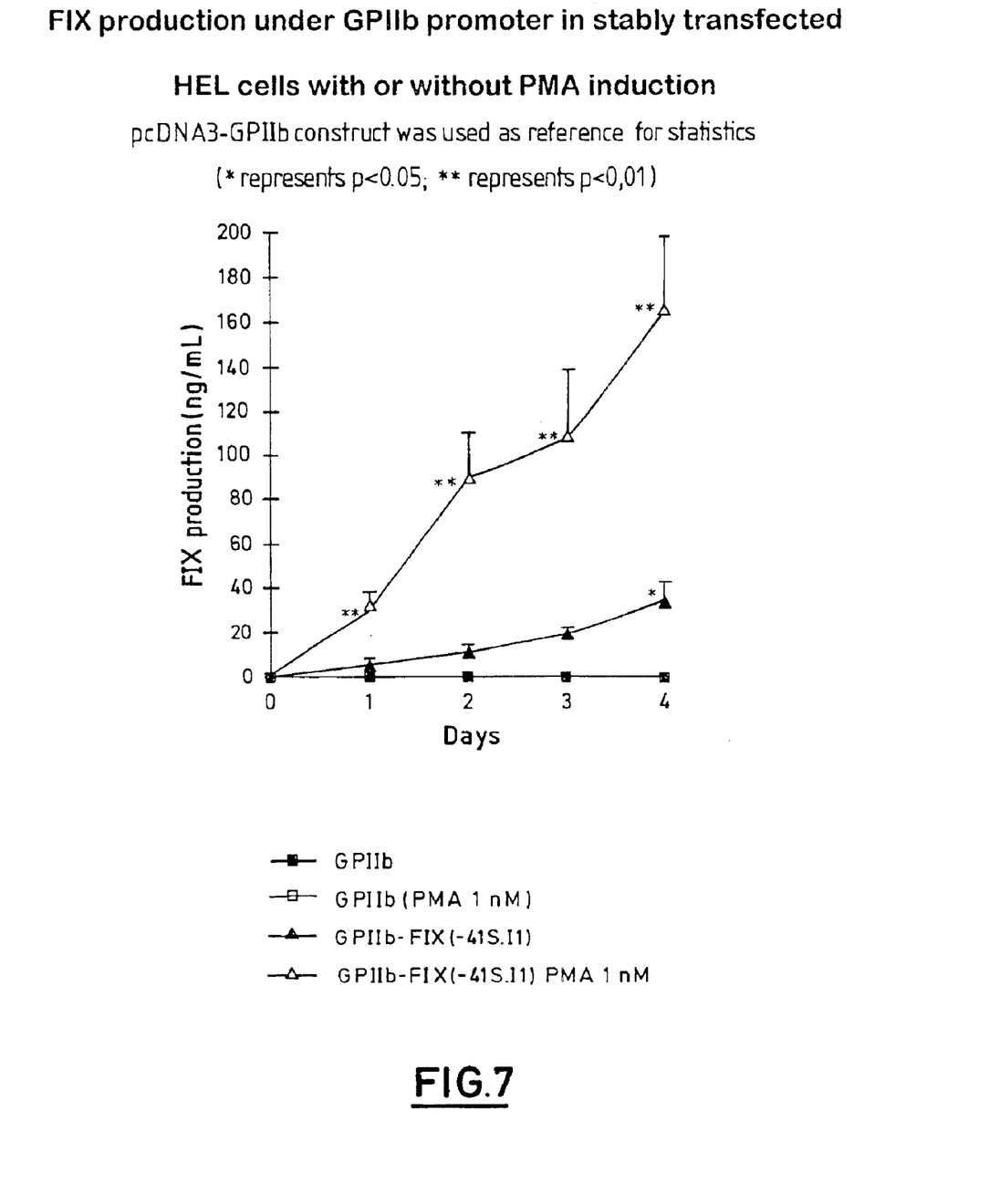
FIG. 7 shows FIX production under GPIIb promoter control in stably transfected HEL cells.

When HEL cells were transfected with pcDNA3-GPIIb vector, no FIX was detected in the conditioned medium. With the GPIIb-FIX(-41S.I1) HEL cells, FIX increased regularly during the 4 days of incubation (FIG. 7). After 4 days of culture, GPIIb-FIX(-41S.I1) pools produced $35.0 \pm 7.8$ ng/ml of FIX in the supernatant. Following PMA induction, the FIX production reached $165.0 \pm 32.52$ ng/ml.

2.3. Procoagulant Activity

Figure 8:
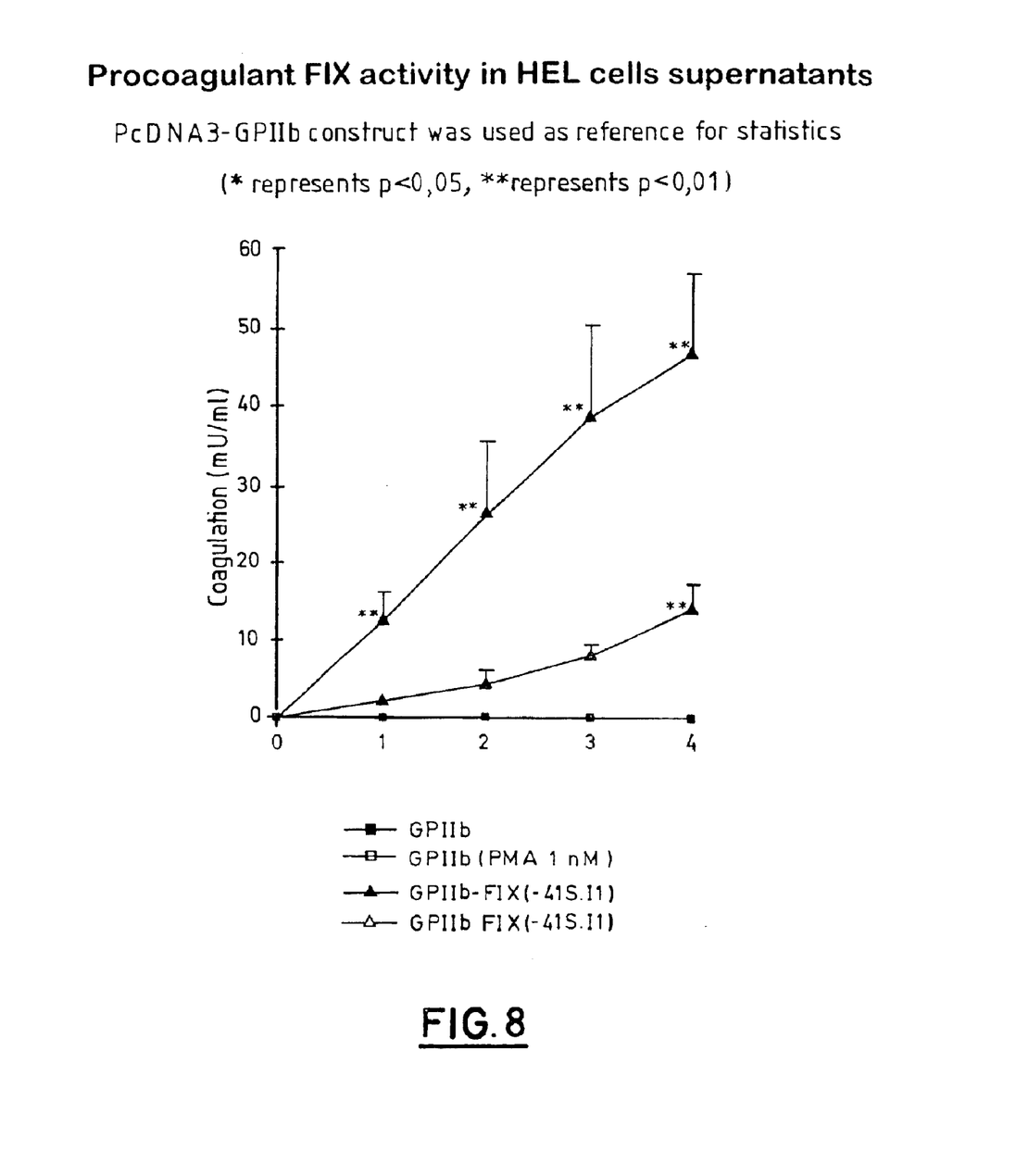
FIG. 8 demonstrates the correlation between FIX procoagulant activity and FIX antigen in the supernatants from HEL cells.

The FIX procoagulant activity was directly correlated with the FIX antigen in the supernatants from HEL cells (FIG. 8). The specific activity of the FIX produced by GPIIb-FIX(-41S.I1)-expressing HEL cells (culture medium: RPMI/1% BSA) was 0.34±0.07 mU/ng.

2.4. FIX Immunoprecipitations

The supernatants of transfected HEL cells were immunoprecipitated and Western blotted to verify the molecular weight of the secreted protein. Purified recombinant Factor IX (Mononine™) was used as control. In the supernatants of pcDNA3-GPIIb expressing cells, no FIX was detected. In the GPIIb-FIX(-41S.I1) HEL cell supernatants without or with PMA induction, one specific band was detected with an approximative molecular weight of 60 kDa. This protein migrated at the same level as immunopurified FIX (Mononine™).

3. Daily FIX Production of FIX(WT) and FIX(WT.I1) Expressing HEL Cells

Figure 9A:
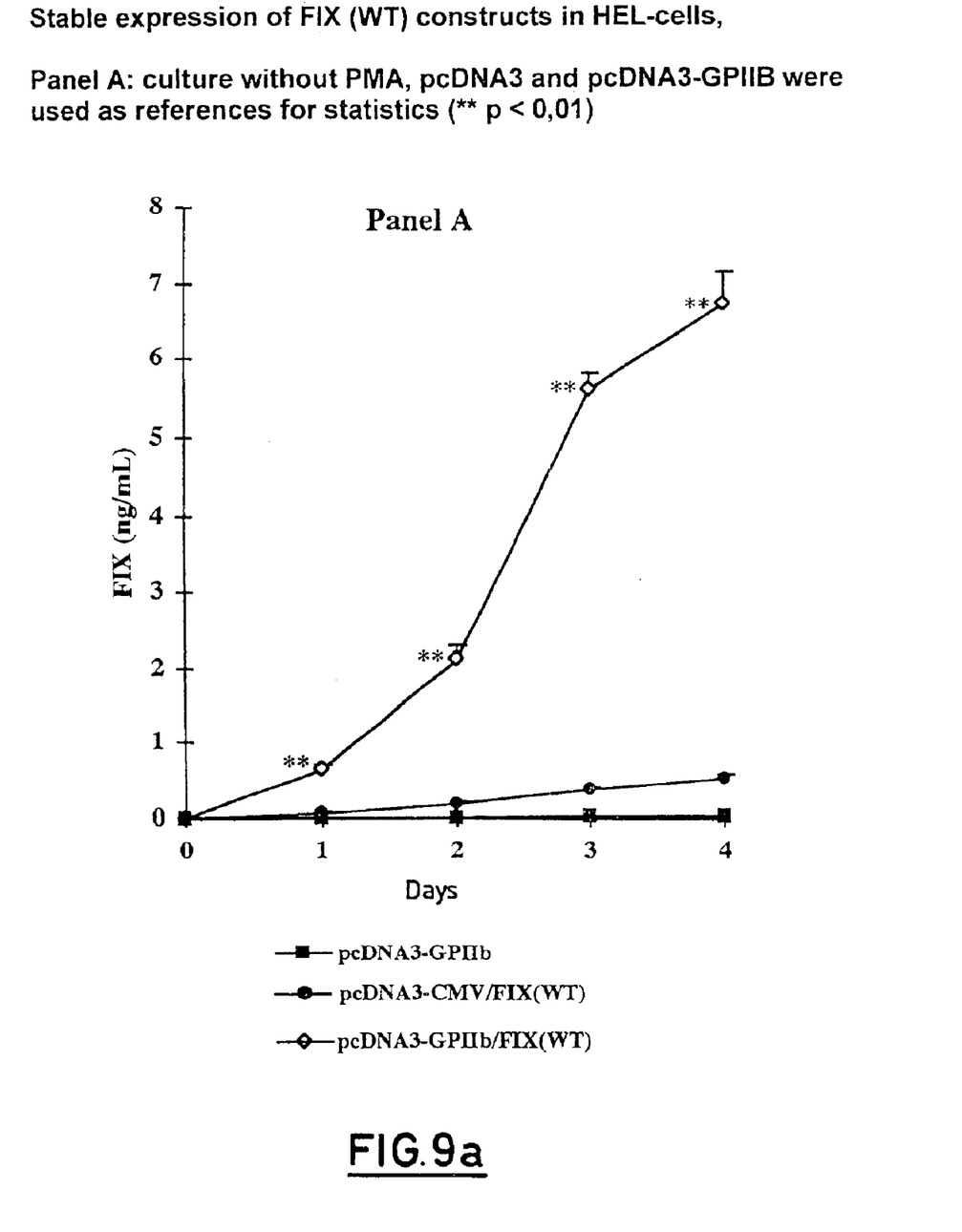
FIG. 9a shows the stable expression of FIX (WT) in HEL cells without PMA induction.
Figure 9B:
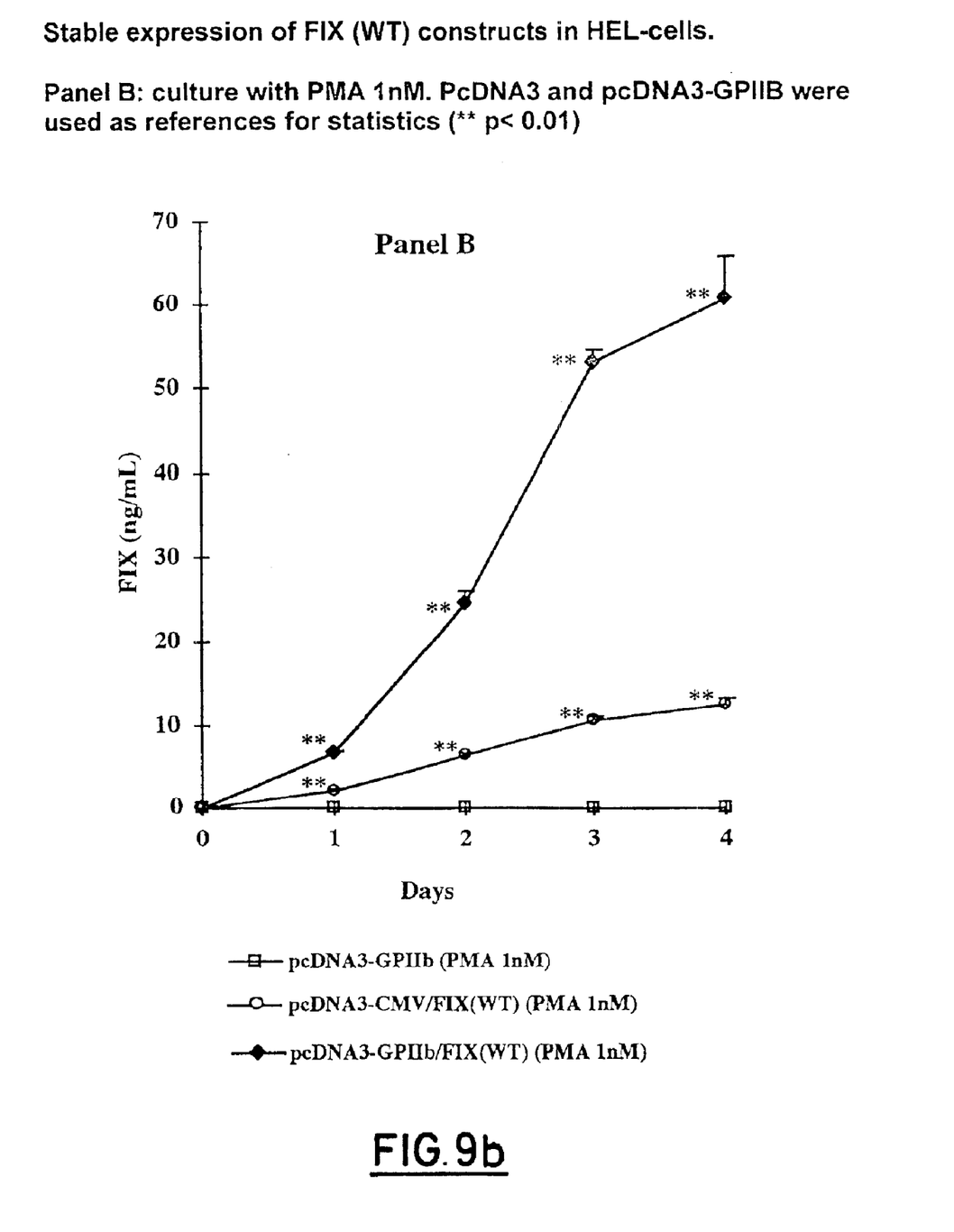
FIG. 9b shows the stable expression of FIX (WT) in HEL cells with PMA induction.

3.1. Comparison of the Efficacy of the CMV and the GPIIb Promoters after Stable Transfections HEL cells were stably transfected with the following constructs: pcDNA3.1 and pcDNA3-GPIIb used as negative controls, GPIIb-FIX(WT), GPIIB-FIX(WT.I1) and also the corresponding CMV constructs (CMV-FIX(WT) and CMV-FIX(WT.I1)). FIG. 9 represents the results obtained with CMV-FIX and GPIIb-FIX HEL cells. As expected, in the two negative controls (pcDNA3 and pcDNA3-GPIIb), no FIX was detected in the supernatants. When the expression of FIX(WT) was directed by the GPIIb promoter, a significantly higher FIX production was measured in the supernatants compared to CMV-FIX. GPIIb-FIX(WT) expressing HEL cells produced about 5 to 10-fold higher amounts of FIX than the HEL cells transfected with CMV-FIX(WT) in the same conditions (±PMA).

3.2. Intron 1 Increases FIX Production

Figure 10:
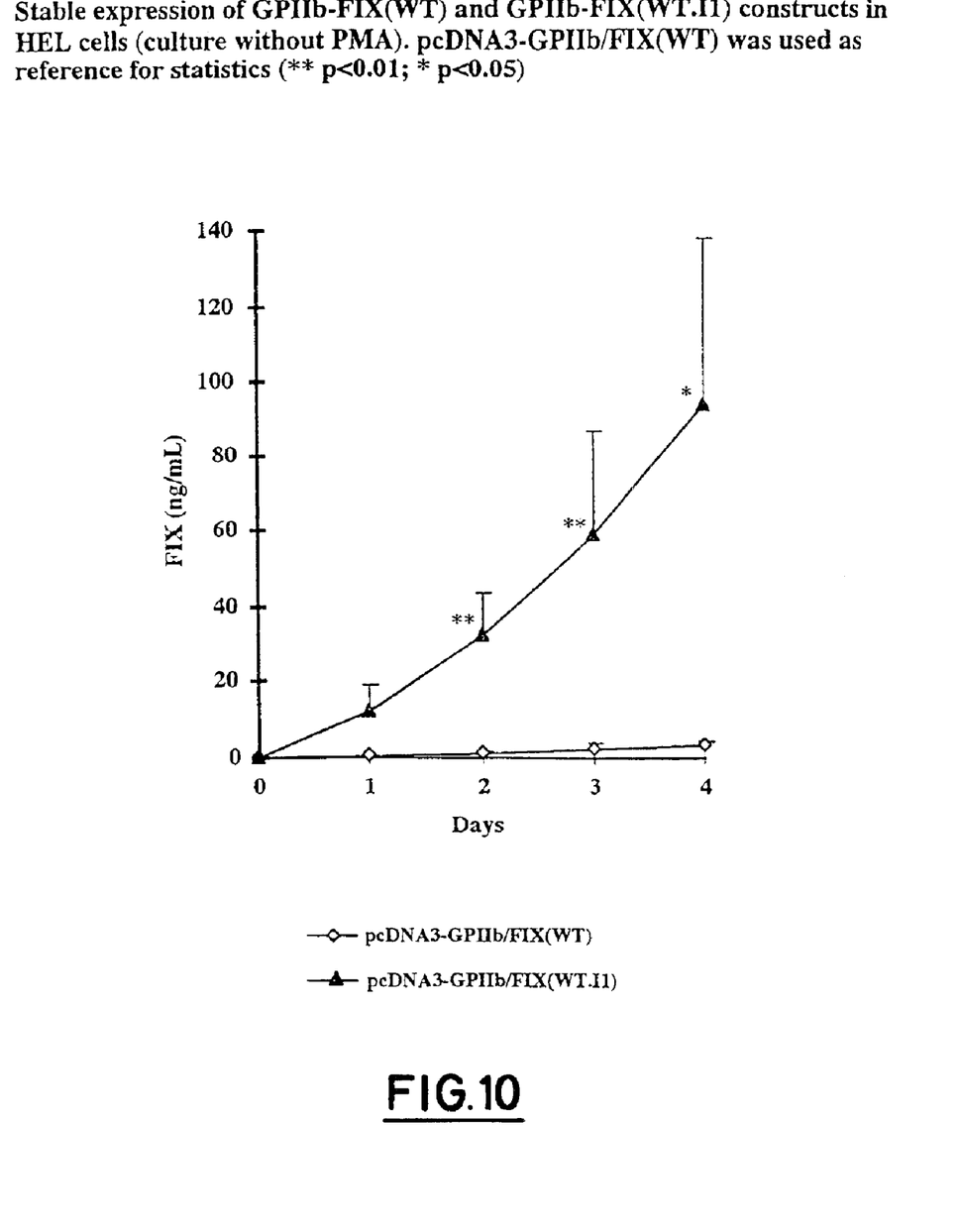
FIG. 10 demonstrates the ability of FIX (WT.I1) directed by the GPIIb promoter to increase FIX production in HEL cells.

We studied the ability of FIX(WT.I1) directed by the GPIIb promoter to increase FIX production in HEL cells. The evaluation of factor IX concentration in the supernatants demonstrated that the highest production was obtained with FIX(WT.I1) construct. Indeed, after 4 days culture, GPIIb-FIX(WT.I1)-transfected HEL cells secreted about 30-fold higher amounts of FIX than the GPIIb-FIX-expressing HEL cells (FIG. 10). When the cells were stimulated with PMA, GPIIbFIX.I1-transfected cells also produced higher FIXC amounts (×12) in comparison with the GPIIb-FIX-expressing cells (Day 4 values: 398.04±94.23 ng/mL versus 32.12±14.85 ng(mL of FIX).

3.3. Characteristics of Recombinant FIX Produced in HEL Cell Supernatant

In order to further characterize the FIX protein in the supernatants of HEL cells, FIX was immunoprecipitated and the samples were subjected to electrophoresis and blotted. In pCDNA3-GPIIb expressing HEL cells, a single unspecific band was detected with the secondary antibody alone. In GPIIb-FIX(WT) and GPIIb-FIX(WT.I1) transfected HEL cells, a specific band was detected at around 60 kDa. This molecular weight was similar to the previously detected FIX(-41SI1), to the control and to the FIX produced by pcDNA3-CMV/FIX(WT.I1)-expressing HepG2 cells. The difference in the intensity of the bands on the immunoblot analysis was directly correlated with the antigen amount presented in FIG. 10.

3.4. FIX Procoagulant Activity and FIX Activation by FXIa

Figure 11:
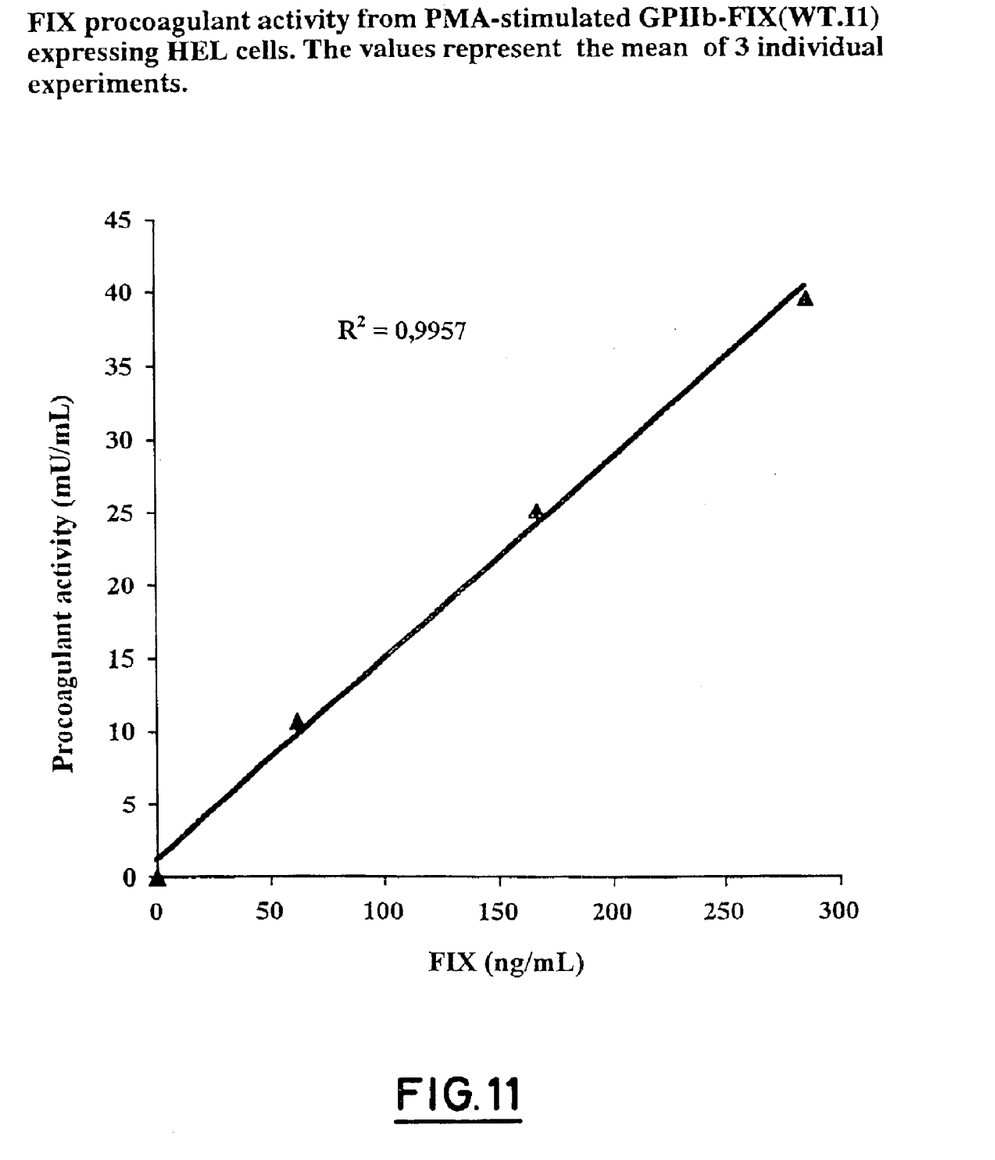
FIG. 11 shows the FIX coagulant activity in the supernatant of HEL cells transfected with GPIIb-FIX(WT.I1) construct after PMA induction.

It was previously shown that FIX needs to be properly processed to be fully active. Factor IX coagulant activity was measured in the supernatant of PMA-stimulated GPIIb-FIX(WT.I1) transfected HEL cells (FIG. 11). The FIX procoagulant activity was directly correlated to the antigen concentration, indicating a correct processing of the molecule. The mean FIX specific activity in the supernatants was 160±69 U/mg. During the coagulation cascade, FIX needs to be activated by FXIa. The FIX cleavage after incubation with FXIa, i.e. activation of the immunoprecipitated FIX from HEL cells resulted in the appearance of two bands corresponding to the heavy chain (29 kDa) and the light chain (19 kDa). The rate of activation and the protein profile from HEL supernatants was similar to the results obtained with Mononine.

3.5. Northern-Blot Analysis

We have shown that the amount of FIX protein produced by HEL cells was closely related to the presence of FIX intron 1 in the FIX cDNA. We have analyzed FIX mRNAs from different transfections of HEL cells. No mRNA hybridized with the FIX mRNA probe in pcDNA3-GPIIb transfected HEL cells without or with PMA induction. In cells transfected with the FIX(WT.I1) constructs, one specific band was detected, which exhibited the correct 1.4 Kb mRNA size. In the GPIIb-FIX(WT) HEL cells, FIX mRNA was detectable following PMA induction only. These mRNAs have the same size than those detected in GPIIb-FIX(WT.I1) HEL cells. The mRNA amounts in the different lysates were directly correlated to the antigen amounts detected in the supernatants, therefore explaining the absence of detection in unstimulated GPIIb-FIX(WT) HEL cells. However, it was confirmed that the expected mRNA was detected in these cells when using larger amounts of total mRNA.

3.1 E. Conclusion

The above-mentioned results show that the hematopoietic cell line HEL can produce and secrete fully active FIX. After transient transfections, the highest production was obtained with CMV-FIX.I1 HEL cells in comparison with the CMV-FIX HEL cells, demonstrating the expression-increasing activity of the FIX intron 1 in this hematopoietic cell line. Using the GPIIb promoter, the FIX production was tissue-specific. Stable transfections have demonstrated that GPIIb promoter was effective in inducing FIX transcription in HEL cells and that FIX intron 1 had an important expression-increasing activity. The secreted FIX protein has a molecular weight of about 60 kDa, similar to the FIX contained in Mononine™ and then seems to undergo a normal maturation process. Finally, the FIX coagulant activity using a one-stage clotting assay corresponded to the FIX antigen. The protein profile after FXIa activation was similar to the profile obtained with Mononine, indicating that the recombinant molecule was fully active. These results obtained with HEL cells reinforce the hypothesis that FIX protein can be produced by CD34+ hematopoietic stem cells.

REFERENCES

Kurachi K, Kurachi S. Regulation mechanism of the Factor IX gene. Thrombosis and Haemostasis 1995, 73, 333–339.

Salier JP, Hirosawa S, Kurachi K. Functional characterization of the 5'regulatory region of the human factor IX gene. J. Biol. Chem. 1990, 265, 7062–7068.

Camerino G, Grzeschik KH, Jaye M, De La Salle H, Tolstoshev P, Lecocq JP, Hellig R, Mandel JL. Regional localization on the human X chromosome and polymorphism of the coagulation factor IX gene (hemophilia B locus). Proc. Natl. Acad. Sci USA 1984, 81, 498502.

Boyd Y, Buckle VJ, Munro EA, Migeon BR, Craig IW. Assignment of the hemophilia B (factor IX) locus to the q26-qter region of the X chromosome. Ann. Hum. Genet. 1984, 48, 145–152.

Yoshitake S, Schach B, Foster DC, Davie EW, Kurachi K. Nucleotide sequence of the gene for human factor IX (antihemophilic factor B). Biochemistry 1985, 24,3736–3750.

Roberts HR. Molecular Biology of the Hemophilia B. Thrombosis and Haemostasis 1993, 70, 1–9.

Nakai H, Herzog RW, Hagstrom JN, Walter J, Kung SH, Yang EY, Tai SJ, Iwaki Y, Kurtzman GJ, Fisher KJ, Colosi P, Couto LB, High KA. Adeno-associated viral vector-mediated gene transfer of human blood coagulation factor IX into mouse liver. Blood 1998, 91, 4600–4607.

White SJ, Page SM, Margaritis P, Brownlee GG. Long-term expression of human clotting factor IX from retrovirally transduced primary human keratinocytes in vivo. Hum. Gene Ther. 1998, 9, 1187–1195.

Baru M, Sha'anani J, Nur I. Retroviral-mediated in vivo gene transfer into muscle cells and synthesis of human factor IX in mice. Intervirology 1995, 38, 356–360.

Wang JM, Zheng H, Blaivas M, Kurachi K. Persistent systemic production of human factor IX in mice by skeletal myoblast-mediated gene transfer: feasibility of repeat application to obtain therapeutic levels. Blood 1997, 90, 1075–1082.

Cherington V, Chiang GG, McGrath CA, Gaffney A, Galanopoulos T, Meriill W, Bizinkauskas CB, Hansen M, Sobolewski J, Levine PH, Greenberger JS, Hurwitz DR. Retroviral vector-modified bone marrow stromal cells secrete biologically active factor IX in vitro and transiently deliver therapeutic levels of human factor IX to the plasma of dogs after reinfusion. Hum. Gene Ther. 1998, 9, 1397–1407.

Hao QL, Malik P, Salazar R, Tang H, Gordon EM, Kohn DB-Expression of biologically active human factor IX in human hematopoietic cells after retroviral vector-mediated gene transduction. Hum. Gene Ther. 1995, 6, 873–880.

Martin P, Papayannopoulou T. HEL cells: a new human erythroleukemia cell line with spontaneous and induced globin expression. Science 1982, 216, 1233–1235.

Tabilio A, Rosa JP, Testa U, Kieffer N, Nurden AT, Del Canizo MC, Breton-Gorius J, Vainchenker W. Expression of platelet membrane glycoproteins and alpha-granule proteins by a human erythroleukemia cell line (HEL). EMBO J. 1984, 3, 453–459.

Long MW, Heffner CH, Williams JL, Peters C, Prochownik EV. Regulation of megakaryocyte phenotype in erythroleukemia cells. J. Clin. Invest. 1990,85, 1072–1084.

Nishizuka Y. The role of protein kinase C in cell surface signal transduction and tumor promotion. Nature 1984, 308, 693–698.

Hong Y, Martin JF, Vainchenker W, Erusalimsky JD. Inhibition of protein kinase C suppresses megakaryocytic differentiation and stimulates erythroid differentiation in HEL cells. Blood 1996, 87, 123–131.

Haas TA, Plow EF. Integrin-ligand interactions: a year in review. Curr. Opin. Cell Biol. 1994, 6, 656–662.

Uzan G, Frachet P, Lajmanovich A, Prandini MH, Denarier E, Duperray A, Loftus J, Ginsberg M, Plow E, Marguerie G. cDNAs clones for human platelet GPIIb corresponding to mRNA from megakaryocytes and HEL cells. Evidence for an extensive homology to other Arg-GlyAsp adhesion receptors. Eur. J. Biochem. 1988, 171, 87–93.

Frachet P, Uzan G, Thevenon D, Denarier E, Prandini MH, Marguerie G. GPIIb and GPIIIa amino acid sequences deduced from human megakaryocyte cDNAs. Mol. Biol. Rep. 1990, 14, 27–33.

Prandini MH, Denarier E, Frachet P, Uzan G, Marguerie G. Isolation of the human platelet glycoprotein lib gene and characterization of the 5'flanking region. Biochem. Biophys. Res. Comm. 1988, 156,595–601.

Bray PF, Rosa JP, Johnston GI, Shiu DT, Cook RG, Lau C, Kan YW, Mc Ever RP, Shuman MA. Platelet glycoprotein IIb. Chromosomal localization and tissue expression. J. Clin. Invest. 1987, 80, 1812–1817.

Uzan G, Prenant M, Prandini MH, Martin F, Marguerie G. Tissue specific expression of the platelet GPIIb gene. J. Biol. Chem. 1991, 266, 8932–8939.

Uzan G, Prandini MH, Beilhier R. Regulation of gene transcription during the differentiation of megakaryocytes. Thromb. Haemost. 1995, 74, 210–212.

What is claimed is:

1. A DNA-construct for the tissue-specific expression of a blood coagulation factor comprising a DNA sequence coding for an amino acid sequence of a blood coagulation factor and a DNA sequence functioning as a promoter which is specific for expression in megakaryocytes, wherein the DNA sequence functioning as a promoter is the DNA sequence for the human platelet glycoprotein IIb (GPIIb) promoter.

2. The DNA-construct as claimed in claim 1, wherein the blood coagulation factor is Factor IX.

3. The DNA-construct as claimed in claim 1, wherein a first truncated intron (Intron 1) of the human FIX gene is inserted into the DNA sequence coding for an amino acid sequence of a blood coagulation factor.

4. A process for the production of a blood coagulation factor in a megakaryocyte cell line comprising:
    transfecting megakaryocyte cells with a DNA-construct coding for a blood coagulation factor comprising:
        a DNA sequence coding for the amino acid sequence of a blood coagulation factor, and
        a DNA sequence functioning as a promoter which is specific for expression in megakaryocytes; and
    expressing the DNA-construct.

5. The process as claimed in claim 4, wherein the production of the blood coagulation factor is stimulated by an inducer.

6. The process as claimed in claim 5, wherein the inducer is phorbol-12-myristate-13-acetate (PMA).

7. The process according to claim 4 wherein the DNA sequence functioning as a promoter is the DNA sequence for the human platelet glycoprotein IIb (GPIIb) promoter.

8. The process according to claim 4, wherein the blood coagulation factor is Factor IX.

9. The process according to claim 4, wherein a first truncated intron (Intron 1) of the human FIX gene is inserted into the DNA sequence coding for an amino acid sequence of a blood coagulation factor.

* * * * *

SEQUENCE LISTING

<160> NUMBER OF SEQ ID NOS: 4

<210> SEQ ID NO 1
<211> LENGTH: 32
<212> TYPE: DNA
<213> ORGANISM: Homo sapiens

<400> SEQUENCE: 1
tggatccttg gagcgcgtga acatgatctt gg            32

<210> SEQ ID NO 2
<211> LENGTH: 37
<212> TYPE: DNA
<213> ORGANISM: Homo sapiens

```
<400> SEQUENCE: 2
tggatccatg cagcgcgtga acatgatcat ggcagaa                               37

<210> SEQ ID NO 3
<211> LENGTH: 674
<212> TYPE: DNA
<213> ORGANISM: Homo sapiens

<400> SEQUENCE: 3
tcaccaccct gtccccagca ctgactgcac tgctgtggcc acactaaagc ttggctcaag      60
acggaggagg agtgaggaag ctgctgcacc aatatggctg gttgaggccg cccaaggtcc     120
tagaaggagg aagtgggtaa atgccatatc caaaaagata cagaagcctc aggttttatc    180
gggggcagca gcttccttct ccttccccga cctgtggcca agtcacaaag caccacagct    240
gtacagccag atgggggaag ggaggagatt agaactgtag gctagagtag acaagtatgg    300
accagttcac aatcacgcta tcccaagcag aaagtgatgg tggcttggac tagcacggtg    360
gtagtagaga tggggtaaag attcaagaga catcattgat aggcagaacc aataggacat    420
ggtaataaac tattctcagg aaaggggagg agtcatggct ttcagccatg agcatccacc    480
ctctgggtgg cctcacccac ttcctggcaa ttctagccac catgagtcca ggggctatag    540
ccctttgctc tgcccgttgc tcagcaagtt acttggggtt ccagtttgat aagaaaagac    600
ttcctgtgga ggaatctgaa gggaaggagg aggagctggc ccattcctgc ctgggaggtt    660
gtggaagaag gaag                                                      674

<210> SEQ ID NO 4
<211> LENGTH: 127
<212> TYPE: DNA
<213> ORGANISM: Homo sapiens

<400> SEQUENCE: 4
ggcccattcc tgcctgggag gttgtggaag aaggaagact agaggatcca ctagtccagt     60
gtggtggaat tctgcagata tccagcacag tggcggccgc tcgagctcag agggcccgtt    120
taaaccc                                                              127
```